United States Patent
Juergens

(10) Patent No.: US 12,048,510 B2
(45) Date of Patent: Jul. 30, 2024

(54) METHOD, SYSTEM, AND SOFTWARE PROGRAM PRODUCT FOR CONTROLLING AN EXCITATION LIGHT SOURCE FOR ENDOSCOPIC FLUORESCENCE IMAGING

(71) Applicant: OLYMPUS Winter & Ibe GmbH, Hamburg (DE)

(72) Inventor: Thorsten Juergens, Hamburg (DE)

(73) Assignee: OLYMPUS WINTER & IBE GMBH, Hamburg (DE)

( * ) Notice: Subject to any disclaimer, the term of this patent is extended or adjusted under 35 U.S.C. 154(b) by 197 days.

(21) Appl. No.: 17/693,768

(22) Filed: Mar. 14, 2022

(65) Prior Publication Data
US 2022/0296101 A1    Sep. 22, 2022

(30) Foreign Application Priority Data
Mar. 22, 2021   (DE) ..................... 10 2021 107 076.7

(51) Int. Cl.
*A61B 5/00*      (2006.01)
*A61B 1/04*      (2006.01)
*G06T 7/00*      (2017.01)

(52) U.S. Cl.
CPC ............ *A61B 5/0071* (2013.01); *A61B 1/043* (2013.01); *G06T 7/0012* (2013.01); *G06T 2207/10064* (2013.01); *G06T 2207/10068* (2013.01); *G06T 2207/20081* (2013.01); *G06T 2207/20084* (2013.01)

(58) Field of Classification Search
CPC .......... A61B 1/000096; A61B 1/00036; A61B 1/00062; A61B 1/00135; A61B 1/0125; A61B 1/043; A61B 1/0655; A61B 2034/2055; A61B 2034/2057; A61B 2090/062; A61B 2090/0811; G06T 2207/20081; G06T 2207/20084
See application file for complete search history.

(56) References Cited

U.S. PATENT DOCUMENTS

| | | |
|---|---|---|
| 6,468,204 B2 | 10/2002 | Sendai et al. |
| 10,799,090 B1 | 10/2020 | Venkataraman |
| 2002/0013512 A1 | 1/2002 | Sendai et al. |

(Continued)

FOREIGN PATENT DOCUMENTS

JP          2004290380 A   * 10/2004   ......... A61B 1/00006

*Primary Examiner* — Aaron B Fairchild
*Assistant Examiner* — Stephen Floyd London
(74) *Attorney, Agent, or Firm* — Scully, Scott, Murphy & Presser, P.C.

(57) ABSTRACT

A method for controlling an excitation light source for endoscopic fluorescence imaging. The method including: one of receiving an excitation light request signal by a switch on an endoscope or generating the excitation light request signal; at least when the excitation light request signal is present, evaluating at least one image detected by the endoscope in real time to determine whether the at least one image originates from inside or from outside of a body; and controlling the excitation light source to only generate excitation light with full power when the excitation light request signal is present and the evaluation indicates that the at least one image originates from inside of the body. Wherein the evaluation of the at least one image is determined by an artificial neural network.

9 Claims, 3 Drawing Sheets

(56) References Cited

U.S. PATENT DOCUMENTS

| | | | |
|---|---|---|---|
| 2012/0053413 A1* | 3/2012 | Yoshida | A61B 1/0638 600/118 |
| 2014/0094649 A1* | 4/2014 | Ito | A61B 1/0669 600/114 |
| 2015/0119639 A1* | 4/2015 | Ebata | A61B 1/00059 600/103 |
| 2016/0213364 A1* | 7/2016 | Inoue | A61B 34/70 |
| 2020/0037864 A1* | 2/2020 | Ushiroda | A61B 1/00188 |
| 2020/0205902 A1* | 7/2020 | Hufford | A61B 1/018 |
| 2021/0015342 A1* | 1/2021 | Venkataraman | G06T 7/70 |

* cited by examiner

METHOD, SYSTEM, AND SOFTWARE PROGRAM PRODUCT FOR CONTROLLING AN EXCITATION LIGHT SOURCE FOR ENDOSCOPIC FLUORESCENCE IMAGING

CROSS-REFERENCE TO RELATED APPLICATION

The present application is based upon and claims the benefit of priority from DE 10 2021 107 076.7 filed on Mar. 22, 2021, the entire contents of which is incorporated herein by reference.

BACKGROUND

Field

The present disclosure relates to a method for controlling an excitation light source for endoscopic fluorescence imaging, a system, and a software program product.

Prior Art

Endoscopic fluorescence measurements are performed in many medical areas of application. In these cases, it is what is known as a special light application, for which, in addition to a light source that generates visible light with a white spectrum, a second light source is required which generates a special light with which the examined tissue can be illuminated for special examination modes. In some cases, one light source that generates both white light and a special light, whether through an integrated second light source or by filtering the white light, may also be sufficient.

Near-infrared fluorescence imaging (NIRF), for example, is typical for this, which can be used to analyze and assess blood vessel perfusion, to confirm the anatomy of the hepatobiliary system, to find lymph nodes or to visualize the ureter following administration of an extrinsic contrast agent such as ICG (indocyanine green), CY5.5, ZW800 or ZW-1. Red dichromatic imaging (RDI) can be used to identify the source of arterial bleeding. Nar-row band imaging (NBI) can help to differentiate between a benign hyperplasia and cancerous tissues or cancer precursors, for example between intestinal polyps of types NICE-1 and NICE-2, in order to decide whether or not a polyp needs to be resected.

During a procedure or an examination, the tissue supplied with fluorescence dye is illuminated with a light suitable for exciting the fluorescence dye, often in the near-infrared range. The excitation light used is adapted to the absorption spectrum of the fluorescence dye. Through the absorption of the excitation light, the fluorescence dye is brought into an energetically higher state and returns spontaneously to the ground state upon emission of a fluorescence deexcitation light with a fluorescence spectrum typical of the fluorescence dye. In applications in a patient's blood, complex molecules are usually used as a fluorescent agent, the deexcitation light of which is usually lower energy, meaning it has longer wave-lengths, than the excitation light.

This deexcitation light can be detected. With suitable image detection and image evaluation, the detected fluorescence images can be overlaid over the tissue images, for example, in a false color representation.

The shift of the spectrum of the deexcitation light compared to the excitation light comes about in that, during the electronic excitation of the molecules out of their ground state, higher vibration states of the excited state are first occupied, which then emit a part of their energy through vibration relaxation before a spontaneous fluorescence deexcitation takes place with which the remaining energy is emitted. Therefore, more energy is exerted for excitation than is emitted during emission. This also means that the light intensity of the excitation light must be very high in order to generate a usable signal of the deexcitation light with a sufficient signal-to-noise ratio to the background. In typical endoscopic applications, the excitation light is therefore usually and most efficiently generated with laser light sources emitting in the near infrared. The laser light is usually guided from the laser light source to the endoscope, or respectively laparoscope, by means of optical waveguides, for example optical fibers.

In laparoscopy, meaning endoscopic examination or respectively treatment in the abdominal cavity, lens laparoscopes are used. For this purpose, one or more openings are made in the abdominal wall, into which trocars are inserted which, with their pipe-shaped tube, keep the respective access open and through which instruments can be introduced into the abdominal cavity from the outside. For this purpose, the abdominal cavity is insufflated in some cases in order to have free access to the organs to be examined or operated on.

Both due to the optical structure of lens laparoscopes and due to the large volume of the abdominal cavity, the required intensity of the excitation light for the purpose of endoscopic fluorescence imaging is so high on the proximal end of lens laparoscopes that it can irreversibly damage the retina of the unprotected eye of a person in the room. Therefore, persons in the examination room or in the operating room must wear safety goggles to minimize the risk of eye damage that can occur when the endoscope used is disconnected from the optical waveguide that guides excitation light from the laser light source to the endoscope while the excitation light is still activated. This problem arises in other types of endoscopes in the same manner.

U.S. Pat. No. 6,468,204 B2 discloses a fluorescence microscopy system configured to detect whether the endoscope is located inside or outside of a body, and to switch the excitation light source accordingly to prevent eye injuries. Multiple different parameters are proposed to perform the detection, such as the detection of a flicker which is typical of room lighting, the detection of a brightness distribution in an endoscopic image, which in the case of images from inside the body, especially in the digestive system, is usually lighter on the edge than in the center of the image. It is also proposed to compare the image brightness or the color spectrum with typical values, or to detect the presence of straight lines in the image. Other proposed measurements relate to physical or chemical parameters such as the light intensity, the temperature, gas measurements, the generation and measurement of magnetic fields or the generation of light as well as the measurement of the transmitted or reflected light, or the measurement of an air volume.

All of these monoparametric measuring methods have their special use cases, but cannot be easily generalized or used for all possibly occurring cases.

SUMMARY

It is therefore an object to decrease the risk of a retinal injury in applications of endoscopic fluorescence imaging further and in a larger number of cases than was previously possible.

Such object can be achieved by a method for controlling an excitation light source for endoscopic fluorescence imaging, in which an excitation light request signal is generated by actuating an activation actuation element on an endoscope or a control device for an endoscope, wherein at least when an excitation light request signal is present, images detected by an endoscope are evaluated in real time as to whether they originate from inside or from outside of a body, wherein the excitation light source is activated such that it only generates excitation light with full power when an excitation light request signal is present and the evaluation indicates that the images originate from inside of a body, wherein the images detected by the endoscope are evaluated by an artificial neural network.

The method is based on the basic idea that image recognition with suitably trained artificial neural networks is superior to conventional image evaluation methods in the classification of objects or situations. Neural networks that have been trained with sufficiently diverse training image material can recognize and correctly classify a significantly higher number of different situations than conventional image evaluation methods, each of which assess only one image parameter, as has been proposed in U.S. Pat. No. 6,468,204 B2, the entire contents of which is incorporated herein by reference.

Training artificial neural networks is an example of machine learning. Such neural networks, such as convolutional neural networks (CNNs), can be used to rapidly recognize structures or objects in images. For this purpose, they are trained using training images or respectively training videos, some of which display the structures that should be recognized later during use. While the training is a very computationally intensive process, the image processing takes place very quickly with the neural network and enables real-time image analysis.

The amount of endoscopic images usually is not currently sufficient to train an artificial neural network exclusively on the basis of endoscopic images. Therefore, a network trained with non-medical or respectively non-endoscopic images can be further trained using endoscopic images, with either all or, less computationally intensive, only the upper layers of the neurons of the neural network being unfrozen for optimization, while the lower layers remain frozen. When the neural network has undergone its initial training with endoscopic images, an additional adaptation can take place to differentiate images from inside of the body from images from outside of the body.

For this purpose, the lower layers of the neural network can be frozen and only the uppermost layers, which form the classifiers, can be unfrozen so that they can be trained on new classifiers such as those for the operating situation or respectively the location of the image. This subsequent training, which can be monitored, then leads to a neural network that stems from the original neural network and achieves good results for the trained application.

In embodiments, the artificial neural network can be configured to classify the images into at least two classes, of which a first class contains images that originate from inside of a body and a second class contains images that originate from outside of a body, wherein images from inside of a trocar can be classified into a third class. In this context, the term trocar is understood to mean the tube of the trocar through which an endoscope is guided. The main classes mentioned above allow an efficient decision as to whether or not the excitation light source may be activated. The addition of a third classification for images from a trocar or respectively its tube can increase the precision of selecting between the classifications for images from inside or outside of a body, respectively.

Images from the tube of a trocar have similarities to both images from inside of the body and from outside of the body, which can lead to the decision of whether an image originates from inside or from outside of a body being erroneous. On the other hand, the images from inside of a trocar have a high conformity, so that a classifier that has been trained on such images from the tube of a trocar has a high recognition reliability. The training of the other two classifiers can then exclude such images so that there is a lower tendency toward erroneous classifications. The involvement of a trocar classifier also enables more extensive measures and a more refined decision logic, such as switching off or on of the excitation light source upon entering or exiting a trocar.

In embodiments, the excitation light source can generate no excitation light or excitation light with reduced power at which damage to the human eye cannot occur when an excitation light request signal is present and the evaluation indicates that the images originate from outside of a body. The excitation light source can generate no excitation light when no excitation light request signal is present.

Completely switching off or blocking the excitation light serves to protect the eyes of the persons present. Alternatively, when excitation light with an intensity that is harmless to the human eye is generated, it can, for example, be visually checked whether the excitation light source is working correctly and all connections and optical light-guides for the transmission of the excitation light to the distal outlet for illuminating light on the endoscope are connected to each other correctly.

In case when it is recognized that images originate from inside of a trocar, the control of the excitation light source can be executed in the same manner in embodiments as when the images originate from outside of a body. This means that no excitation light can be generated inside of a trocar that could leak out through reflection on the inner wall of the trocar.

An evaluation of sequential images can take place when it is recognized that images originate from inside of a trocar, in which it can be determined whether the endoscope is moving through the trocar into the body or out of the body, wherein the excitation light source is deactivated when the endoscope is determined to be moving out of the body. This can take place, for example, in that the diameter of the central opening visible in the image on the distal end of the trocar is determined in sequential images and it is analyzed whether the diameter becomes smaller or grows. In the first case, the endoscope is moving out of the body, in the second case into the body. This measure results in an increased margin for switching the excitation light on or off.

The images can be evaluated at temporal intervals that are short enough that an exposure of the human eye to excitation light has no harmful consequences for the retina. This ensures that the excitation light source can be switched off or the excitation light can be blocked before the exposure of a human eye can lead to irreversible retinal damage.

Such object can also be achieved by a system for endoscopic fluorescence imaging, comprising at least one endoscope, an excitation light source, an image detection device integrated into or proximally placeable onto the endoscope, a controller with an image evaluation device, and an activation actuation element, wherein the controller with the image evaluation device is configured to perform the previously described method.

The system can thus realize the same properties, features, and advantages as the method. For example, the image detection device can comprise a suitably trained artificial neural network that can be used to execute the classification of the images.

Such object can also be solved by a software program product with program code configured to perform the previously described method when run in a controller of the previously described system. For example, the program code can comprise loading the artificial neural network into a region of a data memory, loading the endoscopic images and for classifying the images using the artificial neural network, and generating a signal with which the generation of excitation light is blocked or approved.

BRIEF DESCRIPTION OF THE DRAWINGS

Further features will become evident from the description of embodiments, together with the claims and the appended drawings. Embodiments can fulfill individual features or a combination of several features.

The embodiments are described below, without restricting the general idea of the invention, based on exemplary embodiments in reference to the drawings, whereby we expressly refer to the drawings with regard to the disclosure of all details that are not explained in greater detail in the text. In the drawings.

In the drawings, the same or similar elements and/or parts are, in each case, provided with the same reference numerals such that they are not introduced again in each case.

DETAILED DESCRIPTION

Figure 1:
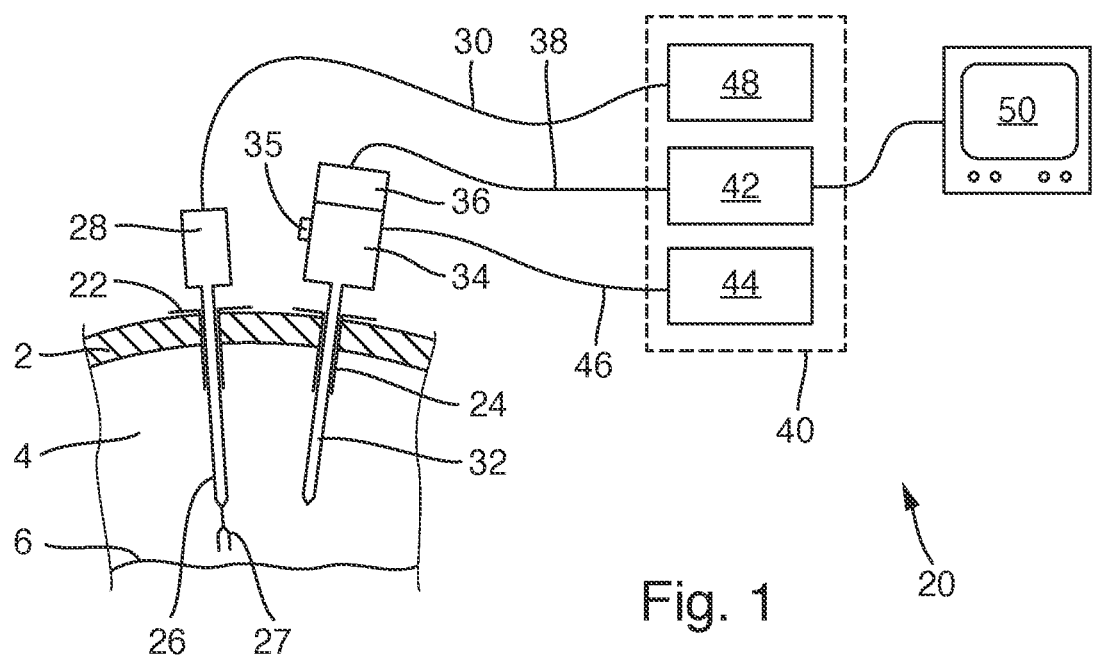
FIG. 1 illustrates a schematic depiction of a system.

FIG. 1 schematically shows a system 20. In the exemplary embodiment shown, the system 20 comprises an HF instrument 26 and an endoscope 32 that are each inserted through their own trocar 22, 24 through an abdominal wall 2 into the insufflated abdominal cavity 4 of a patient. Trocars are instruments used to create a sharp or blunt access to the abdominal or thoracic cavity and to keep it open by means of a tube. The means for opening the access are removed from the tube of the trocar 22, 24 before the HF instrument 26 or respectively the endoscope 32 is inserted into the abdomen from the outside through the tube of the respective trocar 22, 24.

The means for insufflating the abdominal cavity 4 are not shown in FIG. 1. The endoscope 32 serves to illuminate and observe an organ 6 and has a handle 34 with which it can be grasped and operated during the examination. The HF instrument 26 also has a handle 28 and an HF electrode 27 on its distal tip, which is indicated schematically as a bipolar electrode. When HF energy is introduced, tissue can be cut or cauterized with the HF electrode 27 to staunch bleeding. For this purpose, the HF instrument 26 is connected via a supply line 30 to an HF generator 48, which is part of a control system 40.

In the exemplary embodiment shown, the endoscope 32 is configured as a laparoscope. On its handle 34 it has a lateral connection for an optical waveguide 46 via which it is connected to an excitation light source 44 that generates intense excitation light in the infrared range for fluorescence endoscopy. The excitation light source 44 is, for example, an infrared laser. In the inside of the endoscope 32, the excitation light is conveyed to the distal tip, where it exits to illuminate the organ 6. The excitation light source can be configured so as to also generate white illuminating light or to contain a light source for white illuminating light. Both the white illuminating light and the excitation light can then reach the endoscope 32 through the optical lightguide 46. The handle 34 of the endoscope 32 also has an activation actuation element 35, such as a switch, with the actuation of which a user requests that the excitation light source 44 generates excitation light.

On the proximal end, the endoscope 32 has an eyepiece, to which a video head 36 having an image sensor is connected. Via an electrical supply line 38, the video head 36 is connected to a controller 42 of the control system 40, which in addition can also comprise the excitation light source 44 and the HF generator. Many of these components can also be implemented in a control device having a common housing. The controller 42 has an image evaluation unit (not shown), which is configured to process the images captured by the video head 36 and is connected to a display device 50 to display them.

Figure 2:
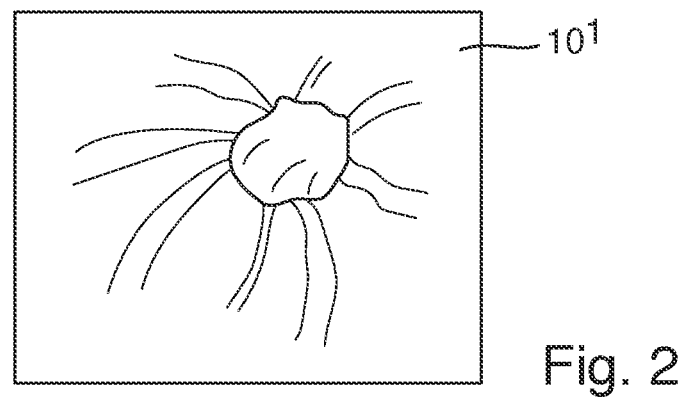
FIG. 2 illustrates an exemplary image captured by an endoscope inside of a body.

FIG. 2 schematically shows a first example of an image $10^1$ that can be captured by an endoscope 32 in the inside of a body. It is, for example, a recording from an intestine, a stomach, or the like. When the tissue shown in image $10^1$ is perfused with blood to which a fluorescence dye has been added, after irradiation with excitation light, it will emit a deexcitation light that can be captured by the endoscope 32 and allows conclusions to be drawn about pathological changes, growths, bleeding, insufficient perfusion, or the like.

Figure 3:
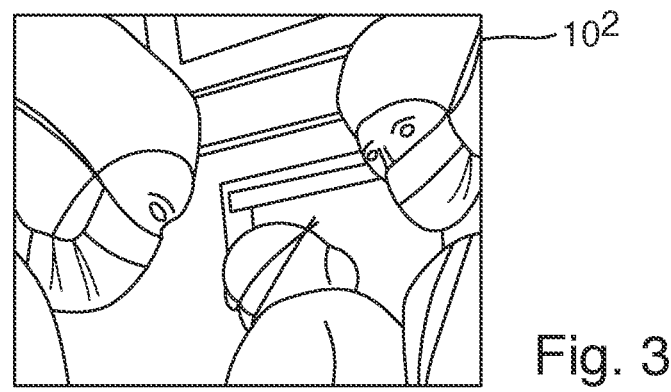
FIG. 3 illustrates an exemplary image captured by an endoscope outside of a body.

FIG. 3 shows another scene in an image $10^2$ in which the endoscope 32 is located outside of a patient. Multiple persons as well as artificial spatial structures such as window frames and the like are located in its field of view. In this environment, it must be ensured that no eye damage can occur due to intense and possibly coherent excitation light. Therefore, given this image, the excitation light source should be prevented from generating excitation light.

Figure 4:
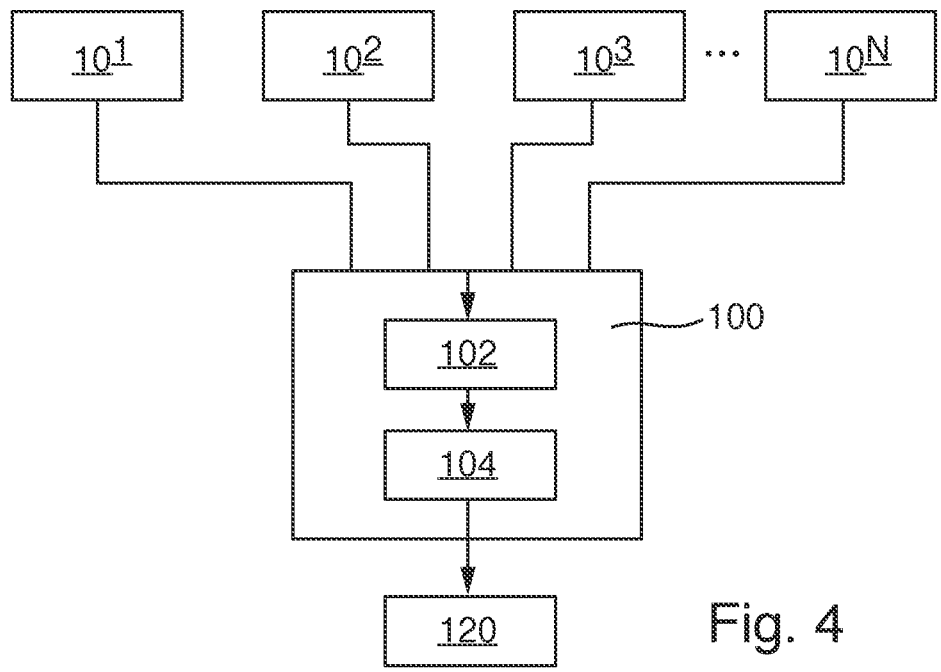
FIG. 4 illustrates a method according to a first embodiment.

FIG. 4 shows a first example of a method. During an endoscopic examination or an endoscopic procedure in which fluorescence imaging should be used, endoscopic images $10^{1, 2, 3, \ldots, N}$ are created. These allow a decision as to whether or not the situation permits the generation of excitation light. For this purpose, the images $10^{1, 2, 3, \ldots, N}$ are subjected to image processing 100 one after the other and in real time, including image recognition 102 and recognition of the locality 104 of the images $10^{1, 2, 3, \ldots, N}$, meaning recognition of whether an image $10^{1, 2, 3, \ldots, N}$ originates from inside or from outside of a body, by an artificial neural network trained for this classification. When excitation light has been requested and it has been established that the situation permits the generation of excitation light, the excitation light source 44 is activated in step 120.

Figure 5:
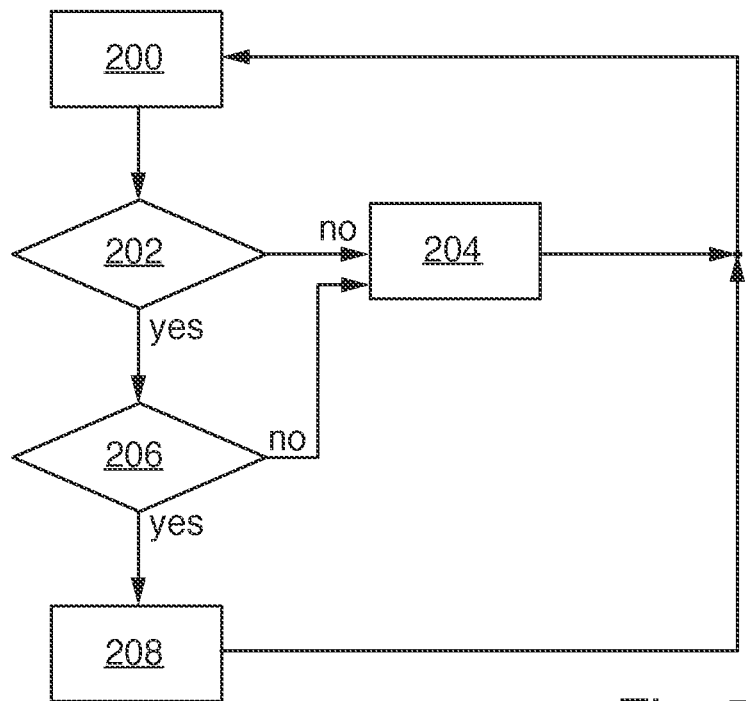
FIG. 5 illustrates a method according to a second embodiment.

FIG. 5 describes a first simple example of the decision process of the image recognition 100 from FIG. 4. In method step 200, an image $10^i$ currently captured by the endoscope 32 is loaded into the image processing unit of the controller 42 and subjected to image recognition or respectively image processing, in which the image data of the image $10^i$ is introduced as input into the artificial neural network in real time. The output of the neural network consists of multiple neurons that serve as classifier output for the decision of whether the image $10^i$ originates from inside or from outside of a body. Consequently, each of the output neurons has an activation value, wherein a high activation value corresponds to a high probability that the image $10^i$ falls into the classification that the respective output neuron represents.

If, as presently, only two or three classifications are available with regard to the decision of whether the image $10^i$ originates from the inside of the body or from outside of the body, and, if applicable, from inside of the tube of the trocar, the classification is chosen whose output neuron has the highest activation potential.

Thus, for the decision step 202, a result exists for whether the image $10^i$ originates from inside ("yes") or from outside ("no") of the body. Depending on this result, either the excitation light source 44 is prevented in method step 204 from generating excitation light if the result was "no," or another decision step 206 follows in the "yes" branch in which it is decided whether an excitation light request signal is present. For this purpose, the activation actuation element must be actuated, for example, on the handle of the endoscope 32 in FIG. 1. If no excitation light request signal is present ("no" branch), the method step 204 is in turn activated, in which the excitation light source 44 is prevented from generating excitation light. Otherwise ("yes" branch), the light source is activated in method step 208.

Regardless of whether the processing of the decision steps has led to method step 204 or to method step 208, the processing then returns to method step 200, in which the next image $10^{i+1}$ is loaded and subjected to the same process.

The method according to FIG. 4 executes the image recognition for each individual image. Alternatives can be implemented in which, for example, the steps 200 and 202 are only performed if an excitation light request signal is present at all. In such a case, the decision tree begins with the decision step 206.

Additionally or alternatively, not every image must necessarily be subjected to image evaluation, but rather it can be sufficient to perform the image evaluation of images from the endoscope 32 at somewhat larger intervals, for example for every second, third, fourth image, etc. In this case, the temporal distance between these images to be evaluated must not be so large that the retina of the human eye could be damaged from unintentional exposure.

Figure 6:
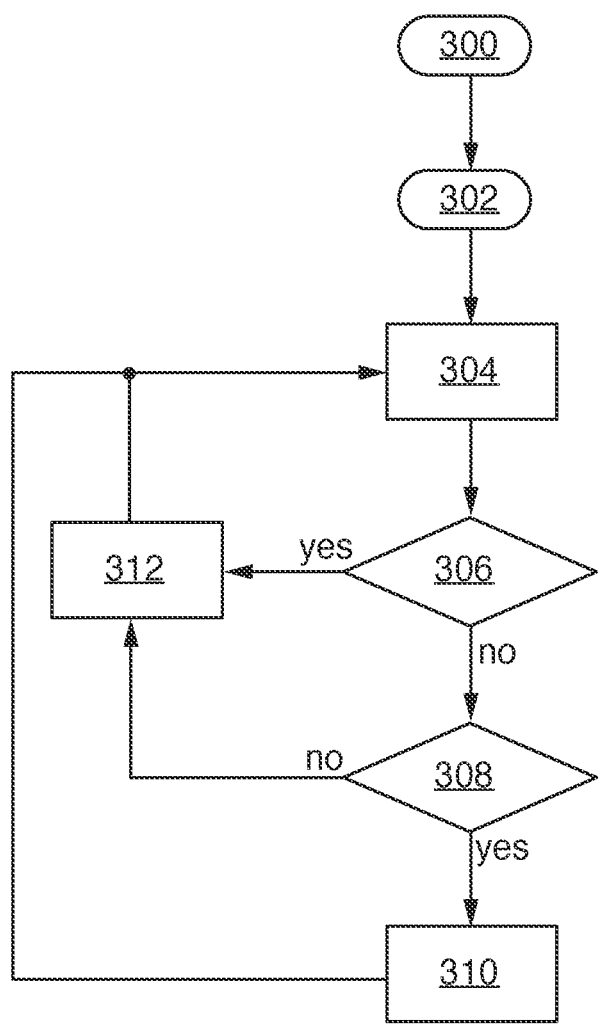
FIG. 6 illustrates a method according to a third embodiment.

FIG. 6 shows another exemplary embodiment of a method. This uses a two-stage locality check and thus implements a somewhat different logic than the method described in FIG. 5.

The method begins with the activation of a light source with white light in step 300. In the course of an endoscopic examination or an endoscopic procedure, the attending physician activates the fluorescence mode in step 302 by actuating, for example, the activation actuation element 35 on the endoscope 32.

When an excitation light request signal is present accordingly, the detected images $10^i$ are analyzed in step 304 by means of a trained artificial neural network. This determines activation potentials of the output neurons for the classifiers that specify probabilities for whether an image $10^i$ originates from outside or from inside of a body.

In the decision step 306, it is first decided whether the images originate from outside of a body. For this purpose, the activation potential of the output neuron of the corresponding classifier is compared with a threshold. If the activation potential exceeds the threshold ("yes" branch), there is a high probability that the image $10^i$ originates from outside of a body and the excitation light source 44 is deactivated in step 312. The process proceeds to step 304 with the following image $10^{i+1}$.

If, however, the excitation potential of the output neuron of the classifier does not reach the specified threshold ("no" branch) in step 306, then a second decision step 308 takes place. In this step, the activation potential of the output neuron of the other classifier, which indicates the probability with which the image originates from the inside of the body, is compared with its own threshold. If this threshold is not reached, the necessary reliability that the endoscope is located in the inside of the body is not great enough to compensate for the risk of causing eye damage. In this case ("no" branch), the excitation light source 44 is also deactivated (step 312). The reliability that the image $10^i$ originates from inside of a body and eye damage can therefore not occur is only high enough to activate the excitation light source in method step 310, when the threshold is exceeded ("yes" branch).

When the image processing of an image $10^i$ has run through this decision tree and either step 310 or step 312 has been applied, the process returns to step 304, where the next image $10^{i+1}$ is loaded and subjected to the same process. This takes place for as long as an excitation light request signal is present.

The process sequences shown in FIGS. 5 and 6 can be extended with a third classifier that serves to recognize whether the distal tip of the endoscope 32 is located in the inside of the tube of a trocar 22, 24 and, if applicable, whether it is being drawn through the tube into the body cavity or out of it. Depending on this, the activation of the excitation light source can be modified. With the introduction of the third classifier for the trocar, it is avoided that the excitation potentials of the two classifiers "in the body" and "outside of the body" can lead to poor results for the special situation in the trocar, such as false positives or false negatives, because the inside of the trocar has characteristics from both situations. The images in the inside of the trocar are, however, characteristic to a high degree, so that the excitation potential of an output neuron of a trocar classifier trained for this is very high and offers a very low error rate when the endoscope 32 is located in the trocar 22, 24.

In the decision tree of the method of FIG. 6, the check of the excitation potential of the output neuron of the trocar classifier could therefore take place before the check of the other two classifiers. Alternatively, the trocar recognition can also be performed subsequently in the event that the excitation potentials of the two other classifiers do not reach their respective thresholds.

While there has been shown and described what is considered to be embodiments of the invention, it will, of course, be understood that various modifications and changes in form or detail could readily be made without departing from the spirit of the invention. It is therefore intended that the invention be not limited to the exact forms described and illustrated, but should be constructed to cover all modifications that may fall within the scope of the appended claims.

LIST OF REFERENCE SIGNS

2 Abdominal wall
4 Abdominal cavity
6 Organ
$10^{1, 2, 3, \ldots, i, i+1, \ldots, N}$ Endoscopic images
20 System
22, 24 Trocar 26 HF instrument
27 HF electrode
28 Handle
30 Supply line
32 Laparoscope
34 Handle
35 Activation actuation element
36 Video head
38 Supply line
40 Control system
42 Controller
44 Excitation light source
46 Optical lightguide
48 HF generator
50 Monitor
100 Image processing
102 Image recognition
104 Recognition of the locality
120 Activation of the excitation light source
200 Loading and image recognition of an image
202 Is image from inside of a body?
204 Block excitation light source
206 Is excitation light request signal present?
208 Activate excitation light source
300 Activation of the light source
302 Activation of fluorescence mode by user
304 Analysis of the detected images
306 Images from outside of a body?
308 Images from inside of a body?
310 Activation of the excitation light source
312 Deactivation of the excitation light source

What is claimed is:

1. A method for controlling an excitation light source for endoscopic fluorescence imaging, the method comprising:
one of receiving an excitation light request signal by a switch on an endoscope or generating the excitation light request signal;
at least when the excitation light request signal is present, evaluating at least one image detected by the endoscope in real time to determine whether the at least one image originates from inside or from outside of a body; and
controlling the excitation light source to only generate excitation light for endoscopic fluorescence imaging with full power when the excitation light request signal is present and the evaluation indicates that the at least one image originates from inside of the body;
wherein the evaluation of the at least one image is determined by an artificial neural network; and
when the evaluation recognizes that the at least one image originates from inside of a trocar, controlling the excitation light source in a same manner as when the at least one image is determined to originate from outside of the body.

2. The method according to claim 1, wherein the artificial neural network is configured to classify the at least one image into at least a first class and a second class, of which the first class contains images that originate from inside of the body and the second class contains images that originate from outside of the body.

3. The method according to claim 2, wherein the artificial neural network is configured to classify the at least one image into a third class containing images that originate from inside of the trocar.

4. The method according to claim 1, further comprising controlling the excitation light source to one of generate no excitation light or excitation light with reduced power when the excitation light request signal is present and the evaluation indicates that the at least one image originates from outside of the body.

5. The method according to claim 1, further comprising controlling the excitation light source to generate no excitation light when the excitation light request signal is not present.

6. The method according to claim 1, wherein,
the at least one image is a plurality of sequential images; and
when an image from the plurality of sequential images is determined to originate from inside of the trocar, the method further comprises:
determining whether the endoscope is moving through the trocar into the body or out of the body, and
deactivating the excitation light source when the endoscope is determined to be moving out of the body.

7. The method according to claim 1, wherein
the at least one image is a plurality of sequential images; and
the evaluating comprises evaluating the plurality of sequential images at temporal intervals with minimal latency.

8. A system for endoscopic fluorescence imaging, the system comprising:
an endoscope;
an excitation light source configured for endoscopic fluorescence imaging,
an image sensor integrated into or proximally placeable onto the endoscope; and
a controller configured to:
one of receive an excitation light request signal by a switch on an endoscope or generate the excitation light request signal;
at least when the excitation light request signal is present, evaluating at least one image detected by the endoscope in real time to determine whether the at least one image originates from inside or from outside of a body; and
controlling the excitation light source to only generate excitation light for endoscopic fluorescence imaging with full power when the excitation light request signal is present and the evaluation indicates that the at least one image originates from inside of the body;
wherein the evaluation of the at least one image is determined by an artificial neural network; and
when the evaluation recognizes that the at least one image originates from inside of a trocar, controlling the excitation light source in a same manner as when the at least one image is determined to originate from outside of the body.

9. A non-transitory computer-readable storage medium storing instructions that cause a computer to at least perform:
one of receiving an excitation light request signal by a switch on an endoscope or generating the excitation light request signal;
at least when the excitation light request signal is present, evaluating at least one image detected by the endoscope in real time to determine whether the at least one image originates from inside or from outside of a body; and
controlling the excitation light source to only generate excitation light for endoscopic fluorescence imaging with full power when the excitation light request signal is present and the evaluation indicates that the at least one image originates from inside of the body;
wherein the evaluation of the at least one image is determined by an artificial neural network; and when the evaluation recognizes that the at least one image originates from inside of a trocar, controlling the excitation light source in a same manner as when the at least one image is determined to originate from outside of the body.

* * * * *